US012612376B2

(12) United States Patent
Jacquin et al.

(10) Patent No.: US 12,612,376 B2
(45) Date of Patent: Apr. 28, 2026

(54) PROCESS FOR SYNTHESIZING 5-HYDROXYMETHYLFURFURAL

(71) Applicant: IFP Energies Nouvelles, Rueil-Malmaison (FR)

(72) Inventors: Marc Jacquin, Rueil-Malmaison (FR); Damien Delcroix, Rueil-Malmaison (FR); Kim Larmier, Rueil-Malmaison (FR); Thierry Huard, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 749 days.

(21) Appl. No.: 17/622,283

(22) PCT Filed: Jun. 15, 2020

(86) PCT No.: PCT/EP2020/066525
§ 371 (c)(1),
(2) Date: Dec. 23, 2021

(87) PCT Pub. No.: WO2020/260058
PCT Pub. Date: Dec. 30, 2020

(65) Prior Publication Data
US 2022/0242840 A1 Aug. 4, 2022

(30) Foreign Application Priority Data
Jun. 24, 2019 (FR) ...................................... 1906806

(51) Int. Cl.
*C07D 307/46* (2006.01)

(52) U.S. Cl.
CPC ................................. *C07D 307/46* (2013.01)

(58) Field of Classification Search
CPC .................................................. C07D 307/46
See application file for complete search history.

(56) References Cited

U.S. PATENT DOCUMENTS

| | | | | |
|---|---|---|---|---|
| 4,740,605 | A * | 4/1988 | Rapp .................... | C07D 307/46 |
| | | | | 549/483 |
| 10,421,735 | B2 * | 9/2019 | Souleymanou ...... | C07D 307/50 |
| 10,526,302 | B2 * | 1/2020 | Souleymanou ...... | C07D 307/50 |
| 11,008,298 | B2 * | 5/2021 | Mosier ................. | C07D 307/50 |
| 11,078,173 | B2 | 8/2021 | Denis et al. | |
| 11,261,168 | B2 * | 3/2022 | Jacquin ................ | C07D 307/48 |
| 2021/0053930 | A1 | 2/2021 | Jacquin et al. | |

FOREIGN PATENT DOCUMENTS

| | | |
|---|---|---|
| FR | 3071498 A1 | 3/2019 |
| FR | 3076554 A1 | 7/2019 |
| WO | 19137810 A1 | 7/2019 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Florentino, Synthesis 2011, No. 7, 1106-1112.*
Yoon, Synlett, 2011, No. 2, pp. 0165-0168.*
Jeong,: Journal of Industrial and Engineering Chemistry, vol. 19, No. 4, Jul. 1, 2013.*
Lewkowski, General Papers, ARKIVOC 2001 (i) 17-54.*
Steinbach Energies (Basel, Switzerland) (2018), 11(3), 645/1-645/15.*
Chheda et al: "An overview of dehydration, aldol-condensation and hydrogenation processes for production of iquid alkanes from biomass-derived carbohydrates", Catalysis Today, Elsevier, Amsterdam, NL, vol. 123, No. 1-4, May 19, 2007 (May 19, 2007), pp. 59-70, XP022085575, ISSN: 0920-5861, DOI: 10.1016/J.CATTOD.2006.12.006.
Guo Qiu et al: "Niobium phosphotungstates: excellent solid acid catalysts for the dehydration of fructose to 5-hydroxymethylfurfural under mild conditions", RSC Advances, vol. 8, No. 57, Jan. 1, 2018 (Jan. 1, 2018), pp. 32423-32433, XP055642246, DOI: 10.1039/C8RA05940C.
Xian-Lei Shi et al: "Bifunctional Polyacrylonitrile Fiber-Mediated Conversion of Sucrose to 5-Hydroxymethylfurfural in Mixed-Aqueous Systems", Chemistry—An Asian Journal, vol. 10, No. 3, Jan. 8, 2015 (Jan. 8, 2015), DE, pp. 752-758, XP055642243, ISSN: 1861-4728, DOI: 10.1002/asia.201403338.
Jaewon Jeong et al: "Commercially attractive process for production of 5-hydroxymethyl-2-furfural from high fructose corn syrup", Journal of Industrial and Engineering Chemistry, vol. 19, No. 4, Jul. 1, 2013 (Jul. 1, 2013), Korea, pp. 1106-1111, XP055642256, ISSN: 1226-086X, DOI: 10.1016/j.jiec.2012.12.004.
Caruso T et al: "Bronsted acidity of ceric ammonium nitrate in anhydrous DMF. The role of salt and solvent in sucrose cleavage", Tetrahedron, Elsevier Science Publishers, Amsterdam, NL, vol. 62, No. 10, Mar. 6, 2006 (Mar. 6, 2006), pp. 2350-2356, XP025001632, ISSN: 0040-4020, [retrieved on Mar. 6, 2006], DOI: 10.1016/J.TET.2005.12.001.
Chao Wang et al: "Efficient and selective conversion of sucrose to 5-hydroxymethylfurfural promoted by ammonium halides under mild conditions", Carbohydrate Research, Pergamon, GB, vol. 347, No. 1, Nov. 12, 2011 (Nov. 12, 2011), pp. 182-185, XP028435044, ISSN: 0008-6215, [retrieved on Nov. 19, 2011], DOI: 10.1016/J.CARRES.2011.11.013.
International Search Report PCT/EP2020/066525 dated Jul. 30, 2020 (pp. 1-3).

* cited by examiner

*Primary Examiner* — Nizal S Chandrakumar
(74) *Attorney, Agent, or Firm* — Csaba Henter; MILLEN, WHITE, ZELANO & BRANIGAN

(57) ABSTRACT

The invention relates to a process for the production of a mixture of 5-hydroxymethylfurfural and glucose from a feedstock containing fructose in the presence of at least one polar aprotic solvent and of at least one dehydration catalyst, in which process the reaction temperature is less than 90° C.

10 Claims, No Drawings

PROCESS FOR SYNTHESIZING 5-HYDROXYMETHYLFURFURAL

TECHNICAL FIELD

The invention relates to a particular process for obtaining a mixture of 5-hydroxymethylfurfural and hexoses by conversion of mixtures of different sugars or of oligomers of different sugars, more specifically mixtures of hexoses, and more particularly mixtures of fructose and glucose or mixed oligomers of these two sugars, such as sucrose, into a mixture of sugars and of 5-hydroxymethylfurfural (hereinafter denoted by the abbreviation 5-HMF) in the presence of at least one polar aprotic solvent, and in the presence of one or more catalysts.

PRIOR ART

5-Hydroxymethylfurfural is a compound derived from biomass which can be given economic value in many fields, as precursor of active principles in the pharmaceutical industry, agrochemistry or specialty chemistry. Its advantage in recent years lies in its use as precursor of 2,5-furandicarboxylic acid (FDCA), which is used as substitute for terephthalic acid as monomer in the production of polyester fibers, convenience plastics or also plasticizers.

The production of 5-HMF by dehydration of hexoses has been known for many years and has been the subject of a large number of research studies.

It is in particular known that the different types of hexoses have different reactivities with respect to the formation of 5-HMF. Among the commonest hexoses, fructose is that which makes it possible to achieve the highest yields by reacting at moderate temperatures in the presence of a Brønsted or Lewis acid catalyst, in particular when the reaction solvent is dimethyl sulfoxide (DMSO). For example, the paper *Bull. Chem. Soc. Japan.*, 1980, 53, 3705, describes that 5-HMF yields of 90% are obtained after reaction at 80° C.

It is also known that the cost of hexose feedstocks (such as glucose and fructose) can be very variable according to their local abundance, their ease of extraction and their degree of purification. Glucose is relatively abundant, while fructose must be obtained by isomerization of glucose, for example by means of enzymatic catalysis (Parker et al., Vol. 5(5), pp. 71-78, December 2010, *Biotechnol. Mol. Biol. Rev.*). This isomerization is limited by thermodynamics, a mixture of glucose and fructose is obtained, and the fructose has to be subsequently separated from the residual glucose. Likewise, sucrose, a very abundant disaccharide, consists of a unit of fructose type and of a unit of glucose type. It is possible to produce an equimolar mixture of glucose and fructose by hydrolysis (called invert sugar) but, here again, a separation stage would be required to isolate the fructose. Due to the structural similarities of the sugars, glucose/fructose separation processes make pure fructose feedstocks more expensive, which limits the appeal of processes for the conversion of fructose into 5-HMF.

Under the commonest conditions for the conversion of fructose into 5-HMF at temperatures of greater than 100° C.), glucose is not or only slightly converted into 5-HMF but undergoes decomposition reactions to give heavy polymeric entities (humins). Reaction examples carried out under mild conditions (temperatures of less than 100° C.) show that fructose can nevertheless be converted with good yields (*Chemical Reviews,* 2013, 113, 1499-1597). Nevertheless, these reactions are either carried out in an aqueous solvent with high concentrations of acid catalyst, which is accompanied by rehydration side reactions to give levulinic acid and formic acid, or in solvents of ionic liquid type or deep eutectic solvents, which pose well-known problems for their application on the industrial scale.

The aim of the process according to the present invention is to overcome the disadvantages of the prior art.

Surprisingly, the applicant company has discovered a process for the production of 5-hydroxymethylfurfural (5-HMF) making possible the selective conversion of a fructoside fraction into 5-HMF in the presence of a non-fructoside fraction.

Advantageously, the non-fructoside fraction is weakly detrimentally affected, that is to say weakly converted. Thus, the differences in physicochemical properties between the 5-HMF and the non-fructoside fraction make it possible to facilitate the separation of these two compounds.

Advantageously, the process according to the present invention makes it possible to obtain very good yields of 5-HMF and of unconverted non-fructoside fraction, such as glucose.

Another advantage of the process according to the invention is to facilitate the separation between the 5-HMF and the unconverted non-fructoside fraction which are obtained.

Definitions and Abbreviations

Concentration by weight of 5-HMF, glucose or fructose is understood to mean the ratio of the weight of 5-HMF, glucose or fructose, respectively, to the weight of reaction medium.

Homogeneous catalyst is understood to mean a catalyst which is soluble in the reaction medium.

Heterogeneous catalyst is understood to mean a catalyst which is insoluble in the reaction medium.

Brønsted acid is understood to mean a molecule of the family of the Brønsted acids which can release a proton $H^+$ in the reaction medium.

Inorganic catalyst is understood to mean a catalyst in which the functional group responsible for the catalytic dehydration activity is not bonded to a hydrocarbon chain by a covalent bond.

Inorganic Brønsted acid catalyst is understood to mean a Brønsted acid catalyst which does not contain carbon atoms and which can release a proton $H^+$ in the reaction medium.

Inorganic Lewis acid catalyst is understood to mean a Lewis acid catalyst which contains an atom from the family of metals or lanthanides.

Aprotic solvent is understood to mean a molecule which acts as solvent and all the hydrogens of which are carried by carbon atoms.

Polar solvent is understood to mean a molecule which acts as solvent, the dipole moment $\mu$ of which, expressed in debye units, has a numerical value of greater than or equal to 2.00, measured at 25° C.

Polar aprotic solvent is thus understood to mean a molecule which acts as solvent, all the hydrogens of which are carried by carbon atoms and the dipole moment $\mu$ of which, expressed in debye units, has a numerical value of greater than or equal to 2.00, measured at 25° C.

wt % denotes a percentage by weight.

The term "weakly converted" is understood to mean a non-fructoside fraction which is converted in a proportion of less than 20%, preferably of less than 16%, preferably of between 0% and 15%, preferably between 0.1% and 12.0%, in a way between 0.5% and 10.0%, in a very preferred way between 0.5% and 5.0%.

Subject Matter of the Invention

The invention relates to a process for the production of 5-hydroxymethylfurfural comprising bringing a feedstock containing free fructose, taken as a mixture with any saccharide or polysaccharide entity, i.e. any polysaccharide feedstock containing one or more non-fructoside units and one or more fructoside units, into contact with at least one dehydration catalyst chosen from homogeneous or heterogeneous and organic or inorganic Brønsted acids, in a polar aprotic solvent having a boiling point of less than 300° C., said process being carried out at a temperature of between 50 and 90° C.

Advantageously, the process according to the present invention makes it possible to obtain very good yields of 5-HMF and of unconverted non-fructoside fraction, such as glucose.

Another advantage of the process according to the invention is to facilitate the separation between the 5-HMF and the unconverted non-fructoside fraction which are obtained.

Preferably, the process is carried out at a temperature of between 60 and 85° C., preferably between 60 and 80° C., preferably between 65 and 75° C. and very preferably at 70° C.

Preferably, the dehydration catalyst has a pKa in DMSO of between 0 and 5.0.

Preferably, the polar aprotic solvent has a boiling point of less than 250° C., preferably of less than 200° C.

Preferably, the conversion of the fructoside fraction into 5-HMF is greater than or equal to 70% and the conversion of the non-fructoside fraction is less than or equal to 20%.

Preferably, the feedstock is introduced into at an initial concentration by weight of fructoside unit of greater than 7% by weight, preferably of between 8% and 30% by weight, with respect to the total weight of solvent.

Preferably, the feedstock is introduced at a solvent/feedstock ratio by weight of between 0.1 and 200.

Preferably, the feedstock is chosen from sucrose or a mixture of glucose and fructose.

Preferably, the polar aprotic solvent is chosen from butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate and γ-valerolactone.

Preferably, the polar aprotic solvent is dimethyl sulfoxide.

Preferably, the homogeneous organic Brønsted acid catalysts are chosen from organic acids of general formulae $R'COOH$, $R'SO_2H$, $R'SO_3H$, $(R'SO_2)NH$, $(R'O)_2PO_2H$, $R'OH$, in which R' is chosen from the following groups:

alkyls, preferably comprising between 1 and 15 carbon atoms, which are or are not substituted by at least one substituent chosen from a hydroxyl, an amine, a nitro, a halogen, preferably fluorine, and an alkyl halide, alkenyls, which are or are not substituted by at least one group chosen from a hydroxyl, an amine, a nitro, an oxo, a halogen, preferably fluorine, and an alkyl halide, aryls, preferably comprising between 5 and 15 carbon atoms, which are or are not substituted by a substituent chosen from a hydroxyl, an amine, a nitro, an oxo, a halogen, preferably fluorine, and an alkyl halide, heteroaryls, preferably comprising between 4 and 15 carbon atoms, which are or are not substituted by a substituent chosen from a hydroxyl, an amine, a nitro, an oxo, a halogen, preferably fluorine, and an alkyl halide.

Preferably, which the homogeneous inorganic Brønsted catalysts are chosen from HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(N_{12}O_{40})\cdot xH_2O$, $H_4SiMo_{12}O_{40}$, $H_3PMo_{12}O_{40}$, $(NH_4)_6Mo_7O_{24}\cdot xH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$ and $HIO_3$.

Preferably, the homogeneous organic Brønsted acid catalysts are chosen from formic acid, acetic acid, trifluoroacetic acid, lactic acid, levulinic acid, 2,5-furandicarboxylic acid, methanesulfinic acid, methanesulfonic acid, trifluoromethanesulfonic acid, bis(trifluoromethanesulfonyl)amine, benzoic acid, para-toluenesulfonic acid, 4-biphenylsulfonic acid, diphenyl phosphate and 1,1'-binaphthyl-2,2'-diyl hydrogen phosphate.

Preferably, the dehydration catalyst(s) are introduced in a solvent/catalyst(s) ratio by weight of between 20 and 10 000, in which the weight of solvent corresponds to the total weight of solvent employed in the process.

DETAILED DESCRIPTION OF THE INVENTION

Feedstock

The saccharide feedstock employed in the process according to the invention comprises either a feedstock containing free fructose, taken as a mixture with any saccharide or polysaccharide entity, or any polysaccharide feedstock containing one or more non-fructoside units and one or more fructoside units which can release fructose by one or more hydrolysis stages. Preferentially, the feedstock treated in the process is sucrose or a mixture of glucose and fructose.

Advantageously, the fructose-containing saccharide feedstock comprises fructose in the monomeric, oligomeric or polymeric form.

Feedstock containing free (or monomeric) fructose taken as a mixture with any saccharide entity denotes, for example, syrups of High-Fructose Corn Syrup type containing fructose and glucose in different proportions (glucose/fructose in ratios by weight or molar ratios of 58/42, 45/55, 10/90, for example). Syrup is understood to mean a solution of sugar in water having a concentration of at least 30 wt %, preferably at least 50 wt %, preferably at least 70 wt %.

Polysaccharide feedstock containing one or more non-fructoside units and one or more fructoside units which can release fructose by one or more hydrolysis stages denotes the oligosaccharides and polysaccharides in which at least one monosaccharide unit is fructose. Feedstocks such as sucrose, kestose, fructans, oligofructans or inulin are denoted, for example.

Advantageously, the polysaccharide feedstocks listed above are capable of releasing monomeric fructose by hydrolysis, it being possible for said fructose produced to be converted into 5-HMF in the process according to the invention.

Oligosaccharide more particularly denotes a carbohydrate having the empirical formula $(C_{6m}H_{10m+2}O_{5m+1})(C_{5n}H_{8n+2}O_{4n+1})$, where m and n are integers, the sum of which is between 2 and 6. The monosaccharide units making up said oligosaccharide are identical or different and at least one unit of formula $(C_{6m}H_{10m+2}O_{5m+1})$ is fructose. By extension, polysaccharide denotes a carbohydrate having the empirical formula $(C_{6m}H_{10m+2}O_{5m+1})(C_{5n}H_{8n+2}O_{4n+1})$, where m and n are integers, the sum of which is greater than or equal to 7.

Advantageously, the feedstock contains a mixture of fructoside and glucoside units so that the process according to the invention makes it possible to obtain a mixture of 5-HMF and glucose. For example, in the case where the feedstock is sucrose, the process according to the invention can make it possible to produce an equimolar mixture of 5-HMF and glucose. Likewise, in the case where the feedstock is High-Fructose Corn Syrup, the process according to the invention makes it possible to produce a mixture of 5-HMF and glucose, the stoichiometry of which depends on the composition of the starting High-Fructose Corn Syrup.

The feedstock is advantageously introduced into the process at a solvent/feedstock ratio by weight of between 0.1 and 200.0, preferably between 0.3 and 100.0 and more preferentially between 1.0 and 50.0.

Solvents

The process according to the invention is carried out in the presence of at least one polar aprotic solvent having a boiling point of less than 300° C., preferably of less than 250° C., preferably of less than 200° C. The polar aprotic solvent is advantageously chosen from butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dim ethylformamide, N,N-dimethylacetamide, sulfolane, N-methylpyrrolidone, dimethyl sulfoxide, propylene carbonate and γ-valerolactone. Preferably, the polar aprotic solvent is chosen from acetone, hexamethylphosphoramide, N,N-dimethylformamide, sulfolane, N-methylpyrrolidone, dimethyl sulfoxide, propylene carbonate and γ-valerolactone. Preferably, the polar aprotic solvent is dimethyl sulfoxide (DMSO).

Dehydration Catalyst

According to the invention, the process is carried out in the presence of at least one dehydration catalyst chosen from homogeneous or heterogeneous and organic or inorganic Brønsted acids capable of catalyzing the dehydration of fructose to give 5-hydroxymethylfurfural.

In one embodiment, at least one dehydration catalyst is chosen from homogeneous or heterogeneous organic Brønsted acids capable of catalyzing the dehydration of fructose to give 5-hydroxymethylfurfural.

Preferably, the homogeneous or heterogeneous organic Brønsted acids have a pKa in DMSO of between 0 and 5.0, preferably between 0.5 and 4.0 and in a preferred way between 1.0 and 3.0. Said pKa values are as defined in the paper by F G Bordwell et al. (*J. Am. Chem. Soc.*, 1991, 113, 8398-8401).

Preferably, the homogeneous organic Brønsted acid catalysts are chosen from organic acids of general formulae R'COOH, R'SO$_2$H, R'SO$_3$H, (R'SO$_2$)NH, (R'O)$_2$PO$_2$H, R'OH, in which R' is chosen from the following groups:

alkyls, preferably comprising between 1 and 15 carbon atoms, preferably between 1 and 10 and preferably between 1 and 6, which are or are not substituted by at least one substituent chosen from a hydroxyl, an amine, a nitro, a halogen, preferably fluorine, and an alkyl halide, alkenyls, which are or are not substituted by at least one group chosen from a hydroxyl, an amine, a nitro, an oxo, a halogen, preferably fluorine, and an alkyl halide, aryls comprising between 5 and 15 carbon atoms and preferably between 6 and 12 carbon atoms, which are or are not substituted by a substituent chosen from a hydroxyl, an amine, a nitro, an oxo, a halogen, preferably fluorine, and an alkyl halide, heteroaryls comprising between 4 and 15 carbon atoms and preferably between 4 and 12 carbon atoms, which are or are not substituted by a substituent chosen from a hydroxyl, an acid, an amine, a nitro, an oxo, a halogen, preferably fluorine, and an alkyl halide.

When the catalysts of organic Brønsted acid type are chosen from organic acids of general formula R'—COOH, R' can also be a hydrogen.

Preferably, the organic Brønsted acids are chosen from formic acid, acetic acid, trifluoroacetic acid, lactic acid, levulinic acid, 2,5-furandicarboxylic acid, methanesulfinic acid, methanesulfonic acid, trifluoromethanesulfonic acid, bis(trifluoromethanesulfonyl)amine, benzoic acid, para-toluenesulfonic acid, 4-biphenylsulfonic acid, diphenyl phosphate and 1,1'-binaphthyl-2,2'-diyl hydrogen phosphate. Very preferably, the homogeneous organic Brønsted acid catalyst is chosen from methanesulfonic acid (CH$_3$SO$_3$H) and trifluoromethanesulfonic acid (CF$_3$SO$_3$H).

The heterogeneous organic Brønsted acid catalysts are chosen from ion-exchange resins, in particular from sulfonic acid resins based on a copolymer preferably of sulfonated styrene/divinylbenzene or on a sulfonated tetrafluoroethylene copolymer (such as, for example, the following commercial resins: Amberlyst® 15, 16, 35 or 36, Dowex® 50 WX2, WX4 or WX8, Nafion® PFSA NR-40 or NR-50, or Aquivion® PFSA PW 66, 87 or 98), charcoals functionalized by sulfonic and/or carboxylic groups, or silicas functionalized by sulfonic and/or carboxylic groups. Preferably, the heterogeneous organic Brønsted acid catalyst is chosen from sulfonic acid resins.

In one embodiment, at least one dehydration catalyst is chosen from homogeneous inorganic Brønsted acids capable of catalyzing the dehydration of fructose to give 5-hydroxymethylfurfural.

Preferably, the homogeneous inorganic Brønsted catalysts are chosen from HF, HCl, HBr, HI, H$_2$SO$_3$, H$_2$SO$_4$, H$_3$PO$_2$, H$_3$PO$_4$, HNO$_2$, HNO$_3$, H$_2$WO$_4$, H$_4$SiW$_{12}$O$_{40}$, H$_3$PW$_{12}$O$_{40}$, (NH$_4$)$_6$(N$_{12}$O$_{40}$)·xH$_2$O, H$_4$SiMo$_{12}$O$_{40}$, H$_3$PMo$_{12}$O$_{40}$, (NH$_4$)$_6$ Mo$_7$O$_{24}$·xH$_2$O, H$_2$MoO$_4$, HReO$_4$, H$_2$CrO$_4$, H$_2$SnO$_3$, H$_4$SiO$_4$, H$_3$BO$_3$, HClO$_4$, HBF$_4$, HSbF$_5$, HPF$_6$, H$_2$FO$_3$P, ClSO$_3$H, FSO$_3$H, HN(SO$_2$F)$_2$ and HIO$_3$. Preferably, the inorganic Brønsted acids are chosen from HCl, HBr, HI, H$_2$SO$_4$, H$_3$PO$_4$ or HNO$_3$. Very preferably, the inorganic Brønsted acid is HCl.

The dehydration catalyst(s) are introduced into the reaction mixture in a solvent/catalyst(s) ratio by weight of between 20 and 10 000, preferably between 40 and 2000, preferably between 100 and 1000, in which the weight of solvent corresponds to the total weight of solvent employed in the process.

Implementation of the Process

Said process is carried out at a temperature of between 50 and 90° C., preferably between 60 and 85° C., preferably between 60 and 80° C., preferably between 65 and 75° C., very preferably at 70° C., and preferably at a pressure of between 0.0001 and 8.0 MPa, preferably between 0.001 and 5.0 MPa and in a preferred way between 0.01 and 3.0 MPa.

Without being committed to any theory, the implementation of the process according to the invention at temperatures of less than 90° C. makes it possible to selectively convert the fructoside fraction of the feedstock while retaining the unconverted or weakly converted non-fructoside fraction (for example glucoside fraction).

Preferably, the process makes it possible to achieve conversions of the fructoside fraction into 5-HMF of greater than or equal to 70%, preferably of greater than or equal to 75%, in a preferred way of greater than or equal to 80%. Said conversions of the fructoside fraction are accompanied by a conversion of the non-fructoside fraction of less than or equal to 20%, preferably of less than or equal to 16%, preferably of between 0% and 15%, preferably between 0.1% and 12.0%, in a way between 0.5% and 10.0%, very preferably between 0.5% and 5.0%.

Preferably, the process is carried out for a period of time of between 15 and 300 minutes (min), preferably between 20 and 260 min, preferably between 30 and 240 min, preferably between 30 and 200 min, preferably between 35 and 150 min and very preferably between 45 and 120 min.

The feeding of the saccharide feedstock into the reaction mixture can be carried out according to several forms of introduction of said feedstock.

Preferably, the feedstock is introduced into the process into at an initial concentration by weight of fructoside unit of greater than 7% by weight, preferably of between 8% and 30% by weight (wt), with respect to the total weight of solvent, preferably between 9% and 26% by weight, preferably between 12% and 22% by weight.

In a first embodiment, the feedstock is introduced into the reaction mixture in the solid form, optionally using a suitable device which makes it possible to control the flow rate of feedstock.

Nonlimitingly, this device can be an endless screw or a pneumatic system for the transportation of solid particles. Nonlimitingly, this embodiment is preferred for a feedstock of oligosaccharide or polysaccharide type.

The introduction of a feedstock in the solid form corresponding to sucrose or to kestose, from which fructose is released by hydrolysis, is one possibility. Said introduction can be carried out on one or more occasions, sequentially or else continuously.

In a second embodiment, the feedstock is introduced in the liquid form into the reaction medium in solution in a solvent, known as additional solvent, using a pump which makes it possible to control the flow rate for introduction of the solution containing the feedstock. This embodiment is particularly well suited to a feedstock of monosaccharide type, indeed even oligosaccharide type, which can be dissolved in the additional solvent at high concentrations.

Preferably, the gradual introduction of a feedstock corresponding to a fructose and glucose syrup (of High-Fructose Corn Syrup type) via a pump is carried out. Said introduction can be carried out on one or more occasions, sequentially or else continuously.

Additional Solvent

In a specific embodiment, the process also comprises the use of at least one additional solvent chosen from polar aprotic or protic solvents. Said additional solvent can in particular make possible the dissolution of the feedstock before it is brought into contact with the polar aprotic solvent and the dehydration catalyst according to the invention.

Preferably, said additional solvent is chosen from butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate, γ-valerolactone, water, methanol, ethanol, formic acid and acetic acid.

Preferably, the additional solvent chosen from polar aprotic or protic solvents is acetone, hexamethylphosphoramide, N,N-dimethylformamide, sulfolane, N-methylpyrrolidone, dimethyl sulfoxide, propylene carbonate, γ-valerolactone, water, methanol and ethanol, preferably from N,N-dimethylformamide, sulfolane, N-methylpyrrolidone, dimethyl sulfoxide, water and methanol, and very preferably the additional solvent is chosen from water and dimethyl sulfoxide.

In a third embodiment, the additional solvent used corresponds to all or to a fraction of the reaction mixture. In this scenario, the additional solvent thus contains at least the polar aprotic solvent, at least one dehydration catalyst employed in the process and optionally at least a fraction of unconverted feedstock of the 5-HMF produced. This embodiment advantageously makes it possible to gradually increase the amount of 5-HMF without increasing the volume of additional solvent. This embodiment of the process for the production of 5-HMF is carried out non-continuously.

In a continuous implementation of the process according to the invention, the weight hourly space velocity (flow rate of feedstock by weight/weight of catalysts) is between 0.01 $h^{-1}$ and 5.0 $h^{-1}$ and preferably between 0.02 $h^{-1}$ and 2.0 $h^{-1}$.

Whatever the embodiment of the process employed, the water contained in the reaction mixture is preferably removed by any method known to a person skilled in the art, preferably continuously, in order to maintain a water content of less than 30.0 wt %, with respect to the total weight of solvent, preferably of less than 20.0 wt %, preferably of less than 15.0 wt % and very preferably of less than 10.0 wt %.

Advantageously, the implementation of the process for the production of 5-HMF and glucose makes it possible to obtain a good conversion of the fructose involved, and also an excellent selectivity in favor of 5-HMF, while limiting the conversion of the glucose.

The Products Obtained and Their Method of Analysis

The product selectively obtained by the conversion process according to the invention is 5-hydroxymethylfurfural (5-HMF) and glucose. On conclusion of the reaction carried out in the process according to the invention, the reaction medium is analyzed by high performance liquid chromatography (HPLC) in order to determine the conversion of the fructoside fraction of the feedstock and the content of unconverted glucose and of 5-HMF produced in the presence of an internal standard in order to quantify the undesired products (also known as byproducts), such as levulinic acid, formic acid and any coproduct containing sugars, such as humins. The humins are quantified by difference in carbon balance with the carbon initially introduced.

EXAMPLES

In the examples below, the glucose, fructose and sucrose used as feedstock are commercially available and are used without further purification.

The hydrochloric acid is used in the form of a concentrated 1.0M (mol/l) commercial solution in diethyl ether. The methanesulfonic acid, denoted MSA in the examples, is commercially available and is used without further purification.

The dimethyl sulfoxide, denoted DMSO in the examples, used as polar aprotic solvent, is commercially available and is used without further purification.

The concentrations by weight of the constituents of the reaction mixtures are determined by high performance liquid chromatography (HPLC). Aliquots are withdrawn from the reaction mixture at regular intervals in order to evaluate the composition thereof by HPLC. In the examples below in which the feedstock is sucrose, the degree of conversion of the sucrose is 100%, the sucrose being converted into a mixture of glucose, fructose and their reaction products.

It is understood that one mole of sucrose consists of one mole of glucoside units and one mole of fructoside units.

The degree of conversion of the fructose ($Conv_{FRU}$) is defined as the ratio of the molar concentration of converted fructose to the molar concentration of fructoside units present in the initial feedstock, expressed as %.

The glucose yield ($Yield_{GLu}$) is defined as the ratio of the molar concentration of glucose measured in the samples to the molar concentration of glucoside units present in the initial feedstock, expressed as %.

The 5-HMF yield ($Yield_{HMF}$) is defined as the ratio of the molar concentration of 5-HMF measured in the samples to the molar concentration of fructoside units only present in the initial feedstock, expressed as %.

Example 1 (in Accordance) Conversion of a 1:1 Glucose/Fructose Mixture into 5-HMF and Glucose in the Presence of Hydrochloric Acid at 70° C.

Hydrochloric acid (1.0M (mol/1) in diethyl ether ($Et_2O$)) (5.0 mmol) is added to a solution of glucose (4.5 g, 25.0 mmol) and fructose (4.5 g, 25.0 mmol) in DMSO (41.0 g). The initial fructose concentration by weight is 9.0 wt %. The initial glucose concentration by weight is 9.0 wt %. The catalyst/(glucose+fructose) molar ratio is 0.100. The reaction medium is stirred at 70° C. for 4 hours. The yields at different reaction times are reported in table 1.

TABLE 1

| Time | 30 min | 60 min | 120 min | 240 min |
|---|---|---|---|---|
| $Conv_{FRU}$ | 87.8 | 96.5 | 100 | 100 |
| $Yield_{GLU}$ | 92.2 | 90.7 | 88.1 | 81.5 |
| $Yield_{HMF}$ | 60.1 | 70.4 | 75.1 | 77.4 |

Example 2 (in Accordance) Conversion of Sucrose into 5-HMF and Glucose in the Presence of Hydrochloric Acid at 70° C.

Hydrochloric acid (1.0M in $Et_2O$) (2.65 mmol) is added to a solution of sucrose (9.0 g, 26.3 mmol) in DMSO (41.0 g). The initial sucrose concentration by weight is 18.0 wt %. The catalyst/sucrose molar ratio is 0.100. The reaction medium is stirred at 70° C. for 4 hours. The yields at different reaction times are reported in table 2.

TABLE 2

| Time | 30 min | 60 min | 120 min | 240 min |
|---|---|---|---|---|
| $Conv_{FRU}$ | 91.4 | 97.4 | 100 | 100 |
| $Yield_{GLU}$ | 92.6 | 92.4 | 88.2 | 82.5 |
| $Yield_{HMF}$ | 61.2 | 69.3 | 73.0 | 73.6 |

Example 3 (in Accordance) Conversion of Sucrose into 5-HMF and Glucose in the Presence of Methanesulfonic Acid at 70° C.

Methanesulfonic acid (2.60 mmol) is added to a solution of sucrose (9.0 g, 26.3 mmol) in DMSO (41.0 g). The initial sucrose concentration by weight is 18.0 wt %. The catalyst/sucrose molar ratio is 0.100. The reaction medium is stirred at 70° C. for 4 hours. The yields at different reaction times are reported in table 3.

TABLE 3

| Time | 30 min | 60 min | 120 min | 240 min |
|---|---|---|---|---|
| $Conv_{FRU}$ | 17.6 | 32.4 | 43.3 | 59.5 |
| $Yield_{GLU}$ | 100 | 100 | 100 | 100 |
| $Yield_{HMF}$ | 8.3 | 13.7 | 23.3 | 34.5 |

Example 4 (in Accordance) Conversion of Sucrose into 5-HMF and Glucose in the Presence of Hydrochloric Acid at 50° C.

Hydrochloric acid (1.0M in $Et_2O$) (2.63 mmol) is added to a solution of sucrose (9.0 g, 26.3 mmol) in DMSO (41.0 g). The initial sucrose concentration by weight is 18.0 wt %. The catalyst/sucrose molar ratio is 0.100. The reaction medium is stirred at 50° C. for 4 hours. The yields at different reaction times are reported in table 4.

TABLE 4

| Time | 30 min | 60 min | 120 min | 240 min |
|---|---|---|---|---|
| $Conv_{FRU}$ | 66.9 | 73.5 | 83.7 | 90.8 |
| $Yield_{GLU}$ | 100 | 100 | 92.3 | 94.8 |
| $Yield_{HMF}$ | 25.6 | 37.0 | 48.4 | 58.6 |

Example 5 (in Accordance) Conversion of Sucrose into 5-HMF and Glucose in the Presence of Hydrochloric Acid at 90° C.

Hydrochloric acid (1.0M in $Et_2O$) (2.63 mmol) is added to a solution of sucrose (9.0 g, 26.3 mmol) in DMSO (41.0 g). The initial sucrose concentration by weight is 18.0 wt %. The catalyst/sucrose molar ratio is 0.100. The reaction medium is stirred at 90° C. for 4 hours. The yields at different reaction times are reported in table 5.

TABLE 5

| Time | 30 min |
|---|---|
| $Conv_{FRU}$ | 100 |
| $Yield_{GLU}$ | 84.8 |
| $Yield_{HMF}$ | 74.5 |

Example 6 (not in Accordance) Conversion of Sucrose into 5-HMF and Glucose in the Presence of Hydrochloric Acid at 120° C.

Hydrochloric acid (1.0M in $Et_2O$) (2.63 mmol) is added to a solution of sucrose (9.0 g, 26.3 mmol) in DMSO (41.0 g). The initial sucrose concentration by weight is 18.0 wt %. The catalyst/sucrose molar ratio is 0.100. The reaction medium is stirred at 120° C. for 4 hours. The yields at different reaction times are reported in table 6.

TABLE 6

| Time | 30 min | 60 min | 120 min | 240 min |
|---|---|---|---|---|
| $Conv_{FRU}$ | 100 | 100 | 100 | 100 |
| $Yield_{GLU}$ | 47.5 | 39.0 | 35.9 | 32.1 |
| $Yield_{HMF}$ | 77.2 | 77.9 | 79.0 | 80.8 |

Example 7 (not in Accordance) Conversion of Glucose Alone into 5-HMF in the Presence of Hydrochloric Acid at 70° C.

Hydrochloric acid (1.0M in $Et_2O$) (2.50 mmol) is added to a solution of glucose (4.5 g, 25.0 mmol) in DMSO (45.5 g). The initial glucose concentration by weight is 9.0 wt %. The catalyst/glucose molar ratio is 0.100. The reaction medium is stirred at 70° C. for 4 hours. The yields at different reaction times are reported in table 7.

TABLE 7

| Time | 30 min | 60 min | 120 min | 240 min |
|---|---|---|---|---|
| $Conv_{FRU}$ | — | — | — | — |
| $Yield_{GLU}$ | 90.2 | 83.3 | 72.9 | 59.6 |
| $Yield_{HMF}$ | 0 | 0 | 0 | 0 |

Example 8 (not in Accordance) Conversion of Fructose Alone into 5-HMF in the Presence of Hydrochloric Acid at 70° C.

Hydrochloric acid (1.0M in $Et_2O$) (0.55 mmol) is added to a solution of fructose (2.0 g, 11.1 mmol) in DMSO (20.0 g). The initial fructose concentration by weight is 9.1 wt %. The catalyst/fructose molar ratio is 0.050. The reaction medium is stirred at 70° C. for 4 hours. The yields at different reaction times are reported in table 8.

TABLE 8

| Time | 30 min | 60 min | 120 min | 240 min |
|---|---|---|---|---|
| $Conv_{FRU}$ | 73.2 | 87.4 | 96.0 | 99.2 |
| $Yield_{GLU}$ | — | — | — | — |
| $Yield_{HMF}$ | 49.0 | 61.2 | 71.9 | 76.7 |

In examples 1 to 4 (in accordance) carried out at temperatures of less than or equal to 80° C., the conversion carried out at low temperature makes it possible to obtain good yields of glucose ($Yield_{GLU}$>80%), which is not converted into undesired products, while making it possible to obtain a conversion of fructose into 5-HMF with yields ranging up to 77% under the most effective conditions (examples 1 and 2).

Surprisingly, glucose is converted less rapidly in the presence of fructoside units (examples 1 and 2) than in its absence under the same conditions (example 7). The presence of glucose or of glucoside units does not appreciably affect the yields obtained from fructoside units or fructose (examples 1 and 2 vs. example 8 with fructose alone); on the contrary, the presence of glucose or of glucoside units surprisingly improves the conversion of fructose after 30, 60 or 120 minutes, and also the 5-HMF yield.

In example 5 (in accordance) carried out at a temperature of 90° C., yields of 85% and 75% of glucose and 5-HMF respectively are obtained with short reaction times, but a longer reaction time results in a deterioration in the glucose yield without, however, appreciably improving the 5-HMF yield.

In example 6 (not in accordance) carried out at a temperature of greater than 90° C., in particular than 100° C., the glucose yield does not exceed 50% without the 5-HMF yield being appreciably greater than 75-80%.

In example 7 (not in accordance) carried out at a temperature of 70° C., for 240 minutes, only with glucose, the glucose yield is less than 60% without production of 5-HMF.

In example 8 (not in accordance) carried out at a temperature of 70° C. only with fructose, the fructose yield does not exceed 50% after reaction for 30 minutes with a moderate fructose conversion of 70%.

The invention claimed is:

1. A process for 5-hydroxymethylfurfural, comprising bringing a feedstock of sucrose or a mixture of glucose and fructose into contact with methanesulfonic acid and/or HCl as catalyst in dimethyl sulfoxide as solvent, said process being carried out at a temperature of 50 to 90° C. and which process selectively converts fructoside units of the feedstock in contrast to the glucoside units of the feedstock, and in which the feedstock is introduced in an initial concentration by weight of fructoside units of greater than or equal to 7% by weight with respect to the total weight of the dimethyl sulfoxide.

2. The process as claimed in claim 1, which is carried out at a temperature of 60 to 85° C.

3. The process as claimed in claim 1, in which the conversion of the fructoside fraction into 5-HMF is greater than or equal to 70% and the conversion of the non-fructoside fraction is less than or equal to 20%.

4. The process as claimed in claim 1, in which the feedstock is introduced at a dimethyl sulfoxide/feedstock ratio by weight of 0.1 to 200.

5. The process as claimed in claim 1, in which the methanesulfonic acid as catalyst is introduced in a dimethyl sulfoxide/methanesulfonic acid ratio by weight of 20 to 10 000, in which the weight of dimethyl sulfoxide corresponds to the total weight of dimethyl sulfoxide in the process.

6. The process as claimed in claim 1, in which the catalyst is HCl.

7. The process as claimed in claim 1, in which the feedstock is introduced in an initial concentration by weight of fructoside unit of 8% to 30% by weight, with respect to the total weight of solvent.

8. The process as claimed in claim 1, which is carried out at a temperature of 65 to 75° C.

9. The process as claimed in claim 1, which is carried out at a temperature of 50 to 65° C.

10. The process as claimed in claim 1, in which the catalyst is methanesulfonic acid.

* * * * *